(12) United States Patent
Halberthal et al.

(10) Patent No.: US 9,119,667 B2
(45) Date of Patent: Sep. 1, 2015

(54) DEVICE AND METHOD FOR ATTACHING A TAG TO A TOOL

(75) Inventors: Reuven Halberthal, Tzur Igal (IL); Jacob Poremba, Nes Ziona (IL)

(73) Assignee: HALDOR Advanced Technologies L.T.D., Hod Hasharon (IL)

( * ) Notice: Subject to any disclaimer, the term of this patent is extended or adjusted under 35 U.S.C. 154(b) by 1265 days.

(21) Appl. No.: 12/778,151

(22) Filed: May 12, 2010

(65) Prior Publication Data

US 2011/0277359 A1    Nov. 17, 2011

(51) Int. Cl.
| G08B 23/00 | (2006.01) |
| A61B 19/00 | (2006.01) |
| G06K 7/10 | (2006.01) |
| G06K 19/04 | (2006.01) |
| G06K 19/077 | (2006.01) |
| H01Q 1/22 | (2006.01) |

(52) U.S. Cl.
CPC ............ *A61B 19/44* (2013.01); *G06K 7/10336* (2013.01); *G06K 19/041* (2013.01); *G06K 19/07749* (2013.01); *H01Q 1/2225* (2013.01); *A61B 2019/448* (2013.01); *Y10T 29/49826* (2015.01)

(58) Field of Classification Search
CPC .................. G06K 19/07777; G06K 19/07728; G06K 19/041; G06K 7/10336; G06K 19/07749; G06K 19/07758; G06K 19/07771; H01Q 1/2225; H01Q 1/22; H01Q 1/42; H01Q 7/00
USPC ............ 340/5.92, 578.8, 572.9; 235/375–385
See application file for complete search history.

(56) References Cited

U.S. PATENT DOCUMENTS

| 5,650,596 A | 7/1997 | Morris |
| 5,923,001 A | 7/1999 | Morris |
| 6,366,206 B1 | 4/2002 | Ishikawa et al. |
| 6,703,935 B1 | 3/2004 | Chung |
| 6,777,623 B2 | 8/2004 | Ballard |

(Continued)

FOREIGN PATENT DOCUMENTS

| EP | 2218421 | 8/2010 |
| WO | WO/96/04530 | 2/1996 |
| WO | WO/2010/092570 | 8/2010 |

OTHER PUBLICATIONS

U.S. Appl. No. 09/304881, filed May 4, 1999—inventor: Sharin L. Morris—case was abandon before publication.

(Continued)

*Primary Examiner* — Ojiako Nwugo
(74) *Attorney, Agent, or Firm* — Soroker-Agmon

(57) ABSTRACT

An identification device adapted to be attached to a tool comprising a holder formed as a curved stratum having a C-shaped cross-section, the stratum having at least one opening thereon, and the internal surface of the holder being micro-etched; an identification tag placed within the holder; and hardening material for fixing the identification tag within the holder.

The identification device is created from a holder, shaped as a curved stratum having a C-shaped cross-section and at least one opening thereon, micro-etching the internal surface of the holder; and fixing an identification tag within the holder by a hardening material. Fixing the tag within the holder may comprise placing the holder within a container; filling the holder to about half the height with a hardening material; placing the identification tag within the holder; filling the holder with the hardening material; and hardening the hardening material.

8 Claims, 6 Drawing Sheets

(56) References Cited

U.S. PATENT DOCUMENTS

| | | |
|---|---|---|
| 6,998,541 B2 | 2/2006 | Morris et al. |
| 7,411,506 B2 | 8/2008 | Volpi et al. |
| 2001/0000659 A1 | 5/2001 | Hayashi |
| 2003/0052788 A1 | 3/2003 | Kwong-Tai Chung |
| 2004/0074974 A1* | 4/2004 | Senba et al. ............ 235/492 |
| 2005/0110638 A1* | 5/2005 | Mohr ...................... 340/572.1 |
| 2006/0043179 A1 | 3/2006 | Nycz et al. |
| 2006/0044137 A1 | 3/2006 | Morris |
| 2006/0187059 A1 | 8/2006 | Fabian et al. |
| 2006/0232407 A1 | 10/2006 | Ballard |
| 2007/0007344 A1* | 1/2007 | Inoue et al. ............. 235/435 |
| 2007/0125392 A1 | 6/2007 | Olson, Jr. et al. |
| 2007/0210923 A1* | 9/2007 | Butler et al. ............ 340/572.8 |
| 2007/0247318 A1 | 10/2007 | Pempsell et al. |
| 2007/0257857 A1 | 11/2007 | Marino |
| 2008/0001760 A1 | 1/2008 | Oh et al. |
| 2008/0129629 A1 | 6/2008 | Kimura et al. |
| 2008/0174409 A1 | 7/2008 | Frank |
| 2008/0272913 A1 | 11/2008 | Barnes et al. |
| 2008/0283615 A1* | 11/2008 | Finn ........................ 235/488 |
| 2010/0133297 A1* | 6/2010 | Arett et al. ............. 222/129 |
| 2010/0179822 A1 | 7/2010 | Reppas |
| 2010/0201487 A1 | 8/2010 | Halberthal et al. |
| 2011/0068926 A1* | 3/2011 | Jong et al. ............ 340/573.1 |
| 2011/0209313 A1* | 9/2011 | Padgett et al. ............ 24/68 BT |

OTHER PUBLICATIONS

PCT/US95/09094—filed Jul. 19, 1995 & published on Feb. 15, 1996 WO 1996/04530.

U.S. Appl. No. 11/248,350, filed Oct. 12, 2005 published on Mar. 2, 2006—2006/0044137.

* cited by examiner

DEVICE AND METHOD FOR ATTACHING A TAG TO A TOOL

TECHNICAL FIELD

The present invention relates to attaching a small object to a tool in general, and to attaching an RFID-tag to a metal tool, in particular.

BACKGROUND

There are many environments in which multiple tools and disposables are used, including for example operation rooms, hangars, garages, or the like.

An operation room is a facility in which intrusive operations are performed on patients. Typically, multiple people participate in an operation, including a chief surgeon, sometimes an assistant surgeon, an anesthesiologist, a scrub nurse, and a circulating nurse. The participating personnel members use multiple tools, such as scalpels, forceps, and others, varying according to the surgery being performed.

Intensive efforts are invested in keeping track of all tools and disposables, in order to make sure no tool unintentionally remains inside the patient's body. Therefore careful counting is performed before, during and after the operation.

Counting the tools is a tedious job and requires intensive resources, including mental resources, personnel time and down-time of the operating room. Counting the tools towards the end of an operation also increases the time the patient's body is open with the associated risks.

In addition, counting is not always error-free, and in too many cases tools end up being left within the patient's body, causing severe damages and even death.

Another problem relates to the life cycle of tools. For example, the tools used in an operation have to be sanitized or sterilized prior to further usage. Other constraints may relate to maintenance operations required for the tools, for example, a blade may have to be sharpened after every predetermined number of operations in which it is used. In another example, tools that have been used in an operation performed on a patient with a contiguous disease may require extra sterilization before further usage, or the like. Making sure that each tool is used and maintained properly also imposes expenses and requires resources, including record keeping and tracking, manual labor and the like.

It would be useful to use a computerized system for counting and tracking the tools. However, such system has to uniquely identify each tool. In order to identify tools, a Radio Frequency (RF) identification transducer can be used, which can identify tools by suitable RF tags attached thereto.

However, attaching such tags to tools imposes a number of challenges. Since the tool is used in an operating room, the whole structure, including the tool, the tag and the connection there between have to be biocompatible. Further, the tag and its attachment to the tool have to withstand at least the number of sterilization the tool is required to withstand, so as not to make the tool unusable prematurely. There is thus a need in the art for a biocompatible and sterilization-resistant identification tag to be attached to a surgery tool, and a method for producing such tag and attaching it to a surgery tool.

SUMMARY

An identification device adapted to be attached to a tool and method for generating the same.

A first aspect of the disclosure relates to an identification device adapted to be attached to a tool, comprising: a holder formed substantially as a curved stratum having a C-shaped cross-section, the holder having external surface and internal surface, the stratum having at least one opening thereon, and the internal surface of the holder being micro-etched; an identification tag placed within the holder; and hardening material for fixing the identification tag within the holder. The identification device can further comprise an elevation component placed within the holder such as to avoid exposure of the identification tag. Within the identification device, the hardening material is optionally a bio compatible material. Within the identification device, the identification tag is optionally a radio frequency (RF) identification tag. Within the identification device, the external surface and the internal surface are optionally substantially concentric.

Another aspect of the disclosure relates to a method for producing an identification device, comprising: obtaining a holder, substantially shaped as a curved stratum having a C-shaped cross-section, the holder having an external surface and an internal surface, the stratum having at least one opening thereon; micro-etching the internal surface of the holder; and fixing an identification tag within the holder by a hardening material. Within the method, obtaining the holder optionally comprises: obtaining a rectangular piece having an at least one opening thereon; and curving the rectangular piece so as to form a C-shape. Within the method, micro-etching the internal surface of the holder optionally comprises: attaching a coating layer to the external surface of the holder; exposing the internal surface of the holder to an etching liquid flowing through the holder; and removing the coating layer from the external surface of the holder. Within the method fixing the identification tag within the holder optionally comprises: placing the holder within a container on a curved rim of the holder; filling the holder to about half the height with a hardening material; placing the identification tag within the holder; filling the holder to its height with the hardening material; and hardening the hardening material. The method can further comprise placing an elevation component within the holder before placing the identification tag. The method can further comprise polishing excess hardening material from the identification device. The method can further comprise washing the identification device. Within the method, the identification tag is optionally a radio frequency identification tag. Within the method, the hardening material is optionally a bio compatible material. The method can further comprise attaching the identification device to a tool. Within the method attaching the identification device to a tool optionally comprises: milling the tool at a location determined for the identification device; and welding the identification device to the tool.

BRIEF DESCRIPTION OF THE DRAWINGS

The present invention will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1A:
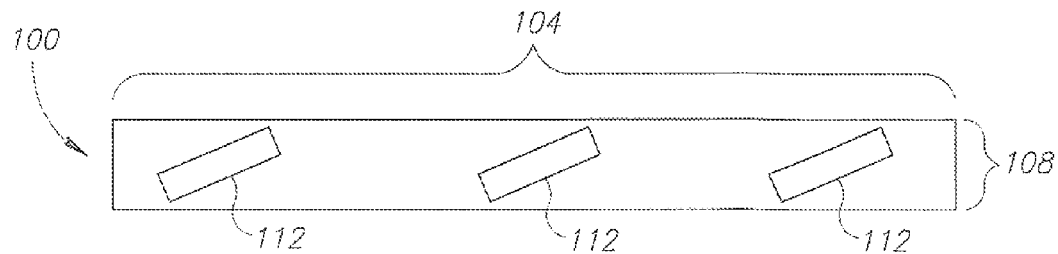
FIGS. 1A and 1B are top views of raw material from which a tag holder is prepared, in accordance with the disclosure.

The disclosure relates to U.S. patent application Ser. No. 12/369,762, filed on Feb. 12, 2009, the full content of which are herein incorporated by reference.

The following disclosure relates to a biocompatible and sterilization-resistant identification tag to be attached to a surgery tool, and a method for attaching such tag to a surgery tool. The communication and identification capabilities are provided by a commercially available tag that can communicate with a corresponding transducer, such as a Radio Frequency (RF) identification tag, for example, SLi-L D8mm Type E from Sokymat Automotive. The tag itself has to be sterilization resistant, and to be able to withstand at least about 200 sterilization cycles so as not to prematurely limit the usability of the tool it is attached to.

In order to attach the tag to a metal tool such as scissors used during surgery, a welding process is required. Therefore, the tag has to be embedded or otherwise constantly inserted into a holder. Such holder must not limit the tag's ability to communicate with the transducer. Further, the exposed parts of the tag must be coated with a biocompatible material, so that if the tag comes in contact with the patient, no harm is done to the tag or the patient.

In some embodiments, the holder is generated from a rectangular metal piece, pressed so as to form a ring. However, a gap is left between the ring's ends, i.e., the ring is "open", in order to enable RF communication between the tag embedded within the ring and the transducer.

In some embodiments, the rectangular metal piece contains holes, slots, or other openings, to provide better resistance to press or other forces and provide better gripping of the material that will fill the ring, as detailed below.

Then the inner part of the open ring may undergo microetching or other roughening, also in order to improve the gripping of the filling material. Micro-etching relates to etching a surface, but not as much as to create an opening thereon, but rather so as to increase its surface area.

In order to place the tag within the holder, the folder is put inside a container so that its rims are parallel to the container bottom, and its gap is perpendicular to the container bottom. Liquid bio-compatible hardening material such as glue is poured until about half the height of the holder, then a solid object used for elevation is placed within the ring so that the tag does not sink to the bottom of the holder, and it is assured that it is not exposed but rather covered on all sides by biocompatible materials, being the bumper of the hardening material. Then the tag itself is placed above the solid object. Then more glue is poured until the glue level reaches the upper rim of the holder.

The whole structure is then heated or undergoes another process that cures the hardening material. After the glue has cured, the holder is polished so as to remove the glue from its external surface and to remove glue exceeding above the holder's top rim. The holder containing the tag is then washed and is ready to be attached to a tool.

In order to attach the holder to the tool, an appropriate location on the tool is determined, so as to minimize the required adaptations. The destination area is corroded or milled so as to prepare the surface of the tool to which the holder will be welded. Preparing the surface includes adaptation as much as possible of the outliner of the tool to the part of the holder that will be attached to the tool, as well as roughing the surface in order to improve the gripping. Once the tool is ready, the holder is welded to the tool.

Figure 1B:
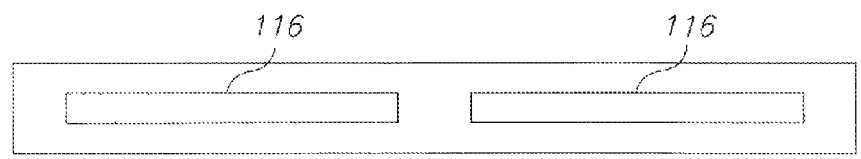

Referring now to FIG. 1A and FIG. 1B, showing top views of two embodiments of the raw material from which the holder is prepared. The holder is generally prepared from a rectangular piece of sterilization-resistant material which has high resistance against corrosion and rust, such as stainless steel SS304L. The L implies that the material is low carbon, which makes it more resistance against corrosion and rust than regular stainless steel. The size of the rectangular piece is determined so as its wide size 104 is slightly smaller than the perimeter of the tag, and its height 108 equals to at least the height of tag plus a few millimeters. The thickness of the rectangular piece is determined so as it is soft enough to be bent, but strong enough not to be misshaped by incidental contact. For example, thickness of about 0.5 mm to 2 mm can be used.

The rectangular piece contains at least one hole, slot, notch or another opening thereon, to increase the mechanical adhesiveness between the metal open ring generated from the rectangular piece and the tag placed therein as detailed below.

In the exemplary embodiments of FIG. 1A and FIG. 1B the rectangular piece indicated 100 is of about 28 mm width by about 3 mm height and is about 0.5 mm thick. These dimensions are appropriate for holding a tag having a radius of about 8.5 mm and height of about 1 mm.

The rectangular piece of FIG. 1A has thereon three diagonal rectangular notches 112, each having dimensions of about 1 mm×about 2 mm. The rectangular piece of FIG. 1B has thereon two horizontal rectangular notches 116, each having dimensions of about 1 mm×about 11 mm.

It will be appreciated that the notch patterns of FIG. 1A and FIG. 1B are exemplary only, and that patterns having different number of notches, or different shapes, sizes or directions of notches can be used as well.

Figure 1C:
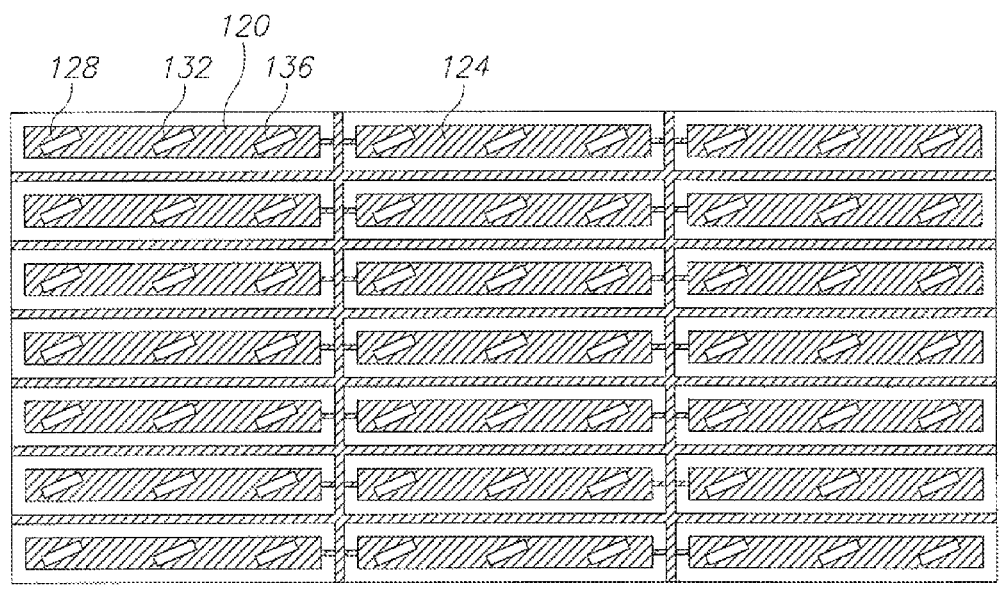
FIG. 1C is a top view of a board from which multiple rectangular pieces for preparing tag holders are produced, in accordance with the disclosure.

Referring now to FIG. 1C, showing a top view of an exemplary embodiment of a board from which multiple rectangular pieces are produced.

The board is initially manufactured as a plain board, having the required thickness for the rectangular pieces such as those shown in FIG. 1A and FIG. 1B above.

A mask having the required shape is placed on each side of the board. The mask is shaped as the rectangular pieces, in which the notches are exposed, and the spaces between the rectangular pieces are exposed as well, excluding thin stripes. After the masks are placed over the two sides of the board, the board and the masks are entered into a liquid which etches the board at all its areas which are not covered by the mask. The board is then washed. Thus, after the etching and washing, the board contains a mesh of rectangular pieces, connected to each other by thin stripes which are easily broken so as to separate the pieces.

Referring now to FIG. 1C, showing a preferred embodiment of the board from which the rectangular pieces are produced. The board comprises a multiplicity of rectangular pieces such as 120, 124. Each rectangular piece has the required notches, slots or other openings, such as notches 128, 132 and 136 of piece 120.

It will be appreciated that a particular board can be masked so as to generate rectangular pieces of various sizes, or various notch patterns.

Once the rectangular pieces are available, each rectangular piece is curved, for example by pressing, so as to round its wide side and create a substantially ring-shaped object. In order to produce the object, the short sides of the piece are brought close to each other, but are not in contact, so as to produce a ring-like object having a gap between its sides. The gap is between about 0.1 mm wide and about 5 mm wide.

The cross section of the holder can be substantially rounded, or it can have any other shape, so as to be easily fit to any tool. However, the holder's area should accommodate the tag.

Figure 2A:
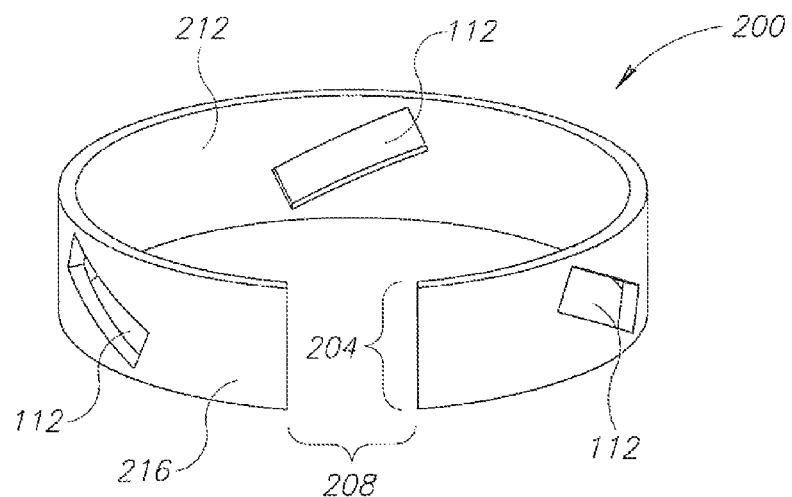
FIG. 2A is a perspective view of a holder, in accordance with the disclosure.

Referring now to FIG. 2A, showing a perspective view of an exemplary holder 200, generally shaped as a curved stratum, such as the rectangular piece of FIG. 1A, and having a cross-section which is substantially C-shaped.

Holder's height 204 is height 108 of the rectangular piece, which is about 3 mm in the exemplary embodiment. Holder 200 is substantially C-shaped, or formed as an open ring, having a radius of about 4.3 mm, and has a gap 208 of about 1 mm between its two ends. The gap is intended to allow radio frequency radiation to reach the tag embedded within the holder. The holder has external surface 216 and internal surface 212.

It will be appreciated that the holder can be produced in other ways and shapes, as long as it can accommodate a relevant identification tag, and has an opening that allows RF communication to and from the identification tag. In some embodiments, the internal and external surfaces of the holder are shaped like a part of a circle, and may be concentric.

In order to micro-etch the holder on its internal surface, it is required to cover the external surface of the holder with a mask.

Figure 2B:
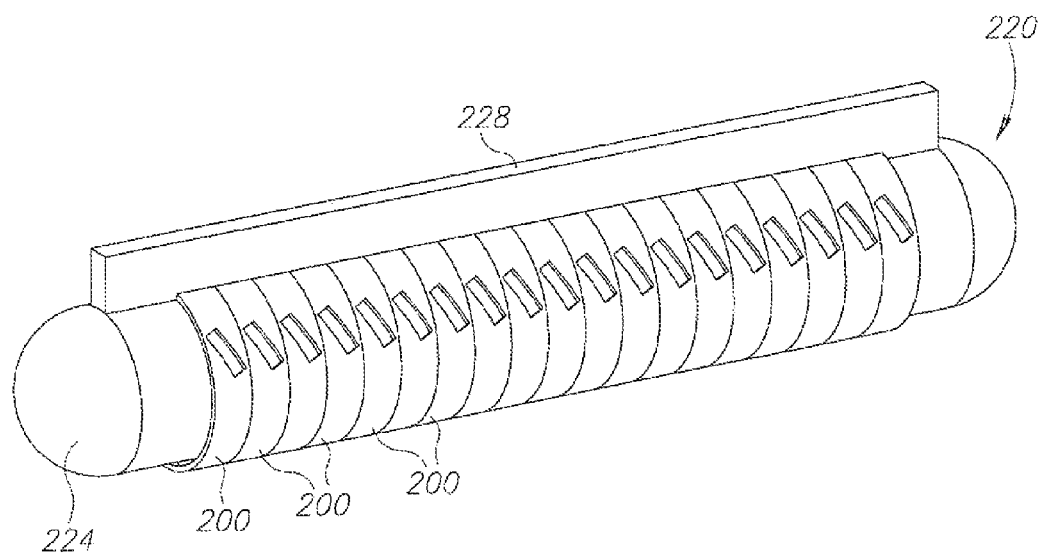
FIG. 2B is a schematic view of an instrument used for masking the external side of holders, with the holders, in accordance with the disclosure.

Referring now to FIG. 2B, showing a schematic view of an exemplary embodiment of an instrument used for masking the external side of holders, with holders placed thereon.

The instrument, generally referenced 220, has a substantially cylindrical body 224 and an elongated protruding part 228 attached to cylindrical body 224. Cylindrical body 224 is shaped such that a cross section taken perpendicularly to the height of the cylinder has the same shape as a cross section taken perpendicularly to the height of holder 200. Protruding part 228 is shaped and located such that its connection to cylindrical body 224 has a width identical to gap 208 of holder 200.

This structure enables the threading of multiple rings such as holders 200 on instrument 220, so that the internal surface of each holder is in full contact with the cylindrical body 224 of instrument 220. It will be appreciated that in some embodiments, holders 200 are placed densely on instrument 220, so that no gap is formed between two adjacent holders.

Instrument 220, together with the holders is coated with glue or any other material that hardens and can then hold the holders together in a shape of a pipe, while covering their external side. Alternatively, instrument 220, together with the holders is covered by a flexible layer, such as a silicone layer which exerts pressure on the holders.

Instrument 220 is then pulled out or otherwise removed, so that the holders form a pipe shape, and their external surface is masked.

It will be appreciated that any other method for holding the holders together in a pipe shape, while covering their external surface can be used.

The holder pipe is then inserted into a container. A liquid capable of etching the material of the holders is flown into the container. The holder pipe is placed in the container such that the liquid flows through the pipe, i.e., the liquid flows in the direction perpendicular to a line connecting one opening of the pipe with the other opening.

In some embodiments the material flown inside the container and used for micro-etching SS304 may contain, for example, sulfuric acid, oxalic acid, or distilled water. When the holders are made of SS304L, the liquid may require the addition of hydrochloric acid to the material used for etching SS304.

The etching material leaves the internal surface of the holders rugged, so that the glue that holds the tag within the holder penetrates into the sponge-like structure and thus has better grip.

After the micro-etching the masking layer covering the external surface of the holders is removed, and the holders are washed.

Once the holder is ready, the tag can be embedded within.

Figure 3A:
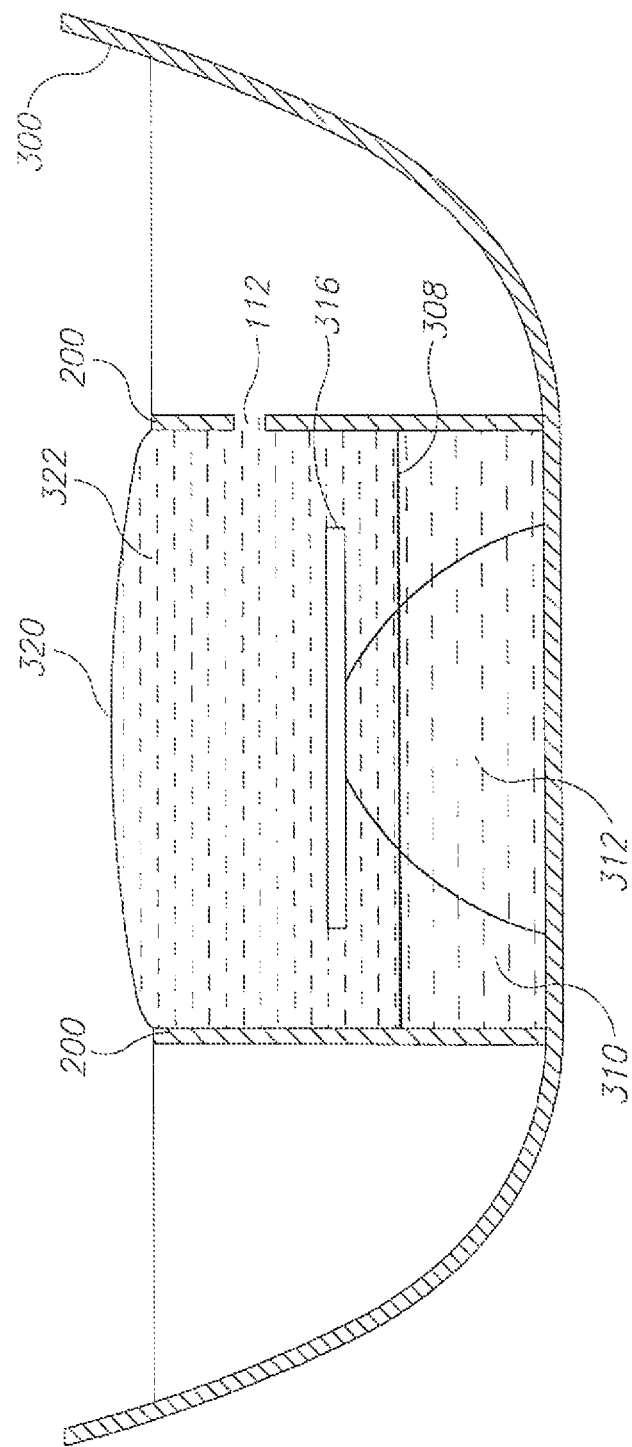
FIG. 3A is a side elevation view of a container for embedding a tag within a holder, in accordance with the disclosure.

Referring now to FIG. 3A, showing a side elevation view of the container used for embedding the tag within the holder, and the used components.

The holder is put in a container 300 which is large enough to contain the holder placed with its rims, which are substantially ring-shaped, being horizontal. FIG. 3A shows the cross section of holder 200 placed within container 300.

The container can be made, for example, of silicone. It will be appreciated that multiple holders can be placed in multiple containers, arranged for example similarly to an egg container.

A biocompatible liquid material, such as Epotek353ND is then poured into holder 200 within the container, until about half the height of the holder. FIG. 3A shows level 308 of the material poured into holder 200, thus creating layer 310.

Then, a solid elevation component such as bumper 312, made of biocompatible material for example the same material as used for creating layer 310 or another material is placed inside the holder, and tag 316 is placed inside the holder on top of bumper 312.

Bumper 312 is required in such cases in which the liquid is thin enough so that the tag will sink to the bottom of the container if elevation is not provided. The bumper is structured such that it can be fully put inside the holder, and its height should be about half the height of the holder placed on its rim. In exemplary embodiments, bumper 312 is shaped substantially like a cone, having height of about 1.5 mm and radius of about 3 mm.

More of the biocompatible liquid is then poured into the holder, up to level 320 at which it covers the top rim of the holder, thus creating layer 322.

It will be appreciated that the glue fills all the available space, including slots or openings 112 of holder 200 and gap 208 (not shown in FIG. 3A) between holder 200s sides.

It will be appreciated that the glue that fills openings 112 creates "handles" which extend into the holder and provide extra gripping of the filling to the holder, without reducing the pressure resistance provided to the holder by the slots. The glue may also pour out through the gap of holder 200. This excess glue is later removed.

Throughout the process of placing the holder in the container and adding the glue, bumper and tag, the glue is maintained in appropriate conditions. For example, when Epotek353ND is used, the container, holder and glue are warmed to a temperature of about 45° C.

After the assembly of the holder, bumper, tag and glue, the container with its content is passed for hardening the liquid. When Epotek353ND is used, hardening can be reached by warming the container to about 80° C. for about half an hour, and then warming it to about 120° C. for about another half an hour. The hardening turns layers 310 and 322 into a single piece of hardened glue, surrounding the identification tag, excluding the area at which the tag is in touch with bumper 312.

When the glue inside the holder is hardened, the external surface of the holder is polished. Due to the surface tension formed on the top side of holder 200 when the glue is poured, the top side of the construction is not an exact plane but is rather dome-like, as indicated by level 320 of FIG. 3A. Therefore, the top side of the construction and optionally the bottom side are polished as well Polishing can be performed, for example, by aluminum oxide polishing device, such as paper covered with aluminum oxide particles. In some embodiments, relatively small particles of aluminum oxide are used, such as P1000 or P1200.

After polishing the holder with the glue, bumper and tag, the holder is washed in order to remove the leftover polishing particles.

At this stage, the holder contains the tag in a stable manner, while not disrupting RF communication between the tag and an RF transducer. The tag is stably embedded within a biocompatible material and wrapped by a metal substantially-ring-shaped holder which has an opening such that it does not form a closed ring, thus enabling the embedded tag to communicate with a transducer. The holder also comprises slots on its external surface to provide better press resistance and better gripping of the biocompatible material to the holder.

Figure 3B:
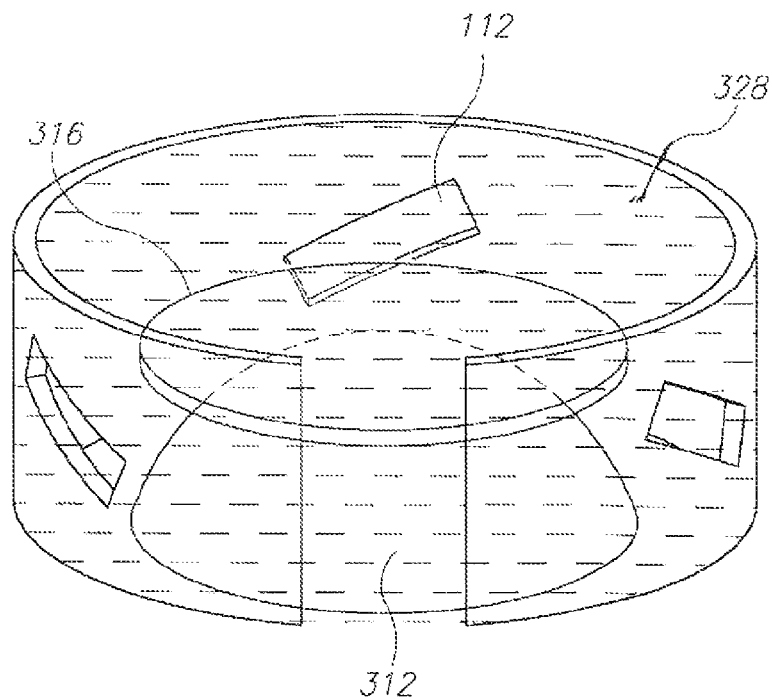
FIG. 3B is a perspective view of a holder with a tag, in accordance with the disclosure.

Referring now to FIG. 3B, showing a perspective view of the holder with the tag. Holder 200, having openings 112 has therein bumper 312 and tag 316. Bumper 312 and tag 316 are fixed within tag 200 by hardening material 328 which was hardened. Hardening material 328 is made up of layer 310 and layer 322 of FIG. 3A.

Figure 3C:
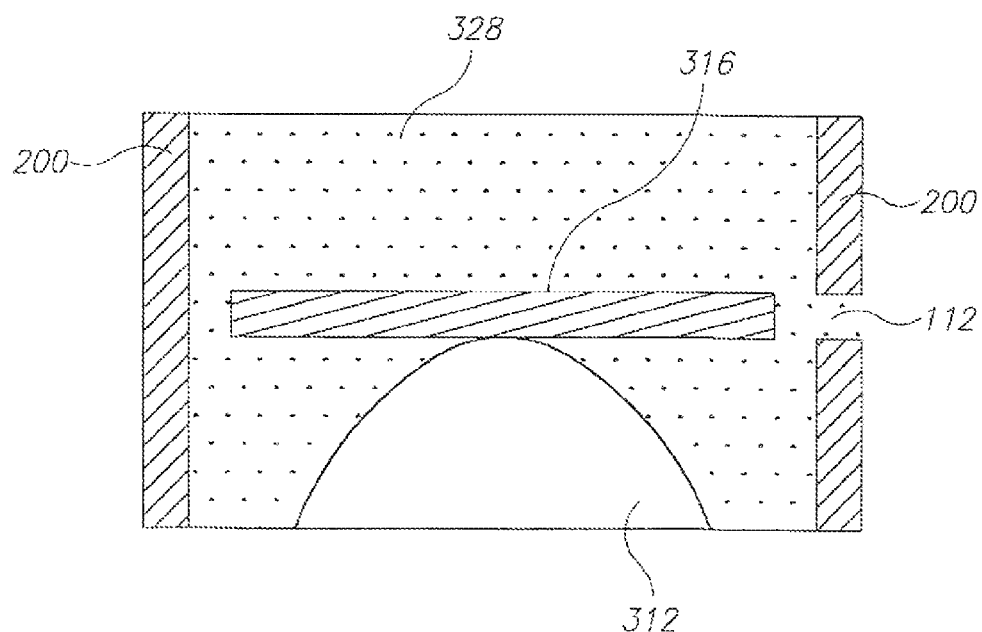
FIG. 3C is an elevation view of the holder and tag, in accordance with the disclosure.

Referring now to FIG. 3C, showing an elevation view of the holder and tag. FIG. 3B shows the sides of holder 200, with opening 112. Within holder 200 is bumper 312, on top of which tag 316 is placed. Bumper 312 and tag 316 are fixated within holder 200 by hardening material 328, which was hardened.

The holder, together with the tag, the hardened glue and the bumper are referred to as an identification device. In order to attach the device to a tool, first a corresponding location on the tool should be determined. The device should be attached such that it will not limit the tool's functionality. Thus, the device should not limit the tool's usage, and should not interfere with operating the tool, or disturb the person operating the tool.

The device should be attached at an area in which the tool's shape is as close as possible to the tool's edge, so that minimum adaptation of the tool is required, and as little as, possible narrow gaps are formed between the tool and the device, for aesthetic reasons as well as for elimination the option for dirt amass there-between.

Therefore, after a location is determined for the tag, the tool is retrofitted. The tool is optionally milled in order to adapt its shape to the shape of the tool, and also for enlarging the contact area. The tool is then rinsed, and the device is welded to the tool.

Figure 4:
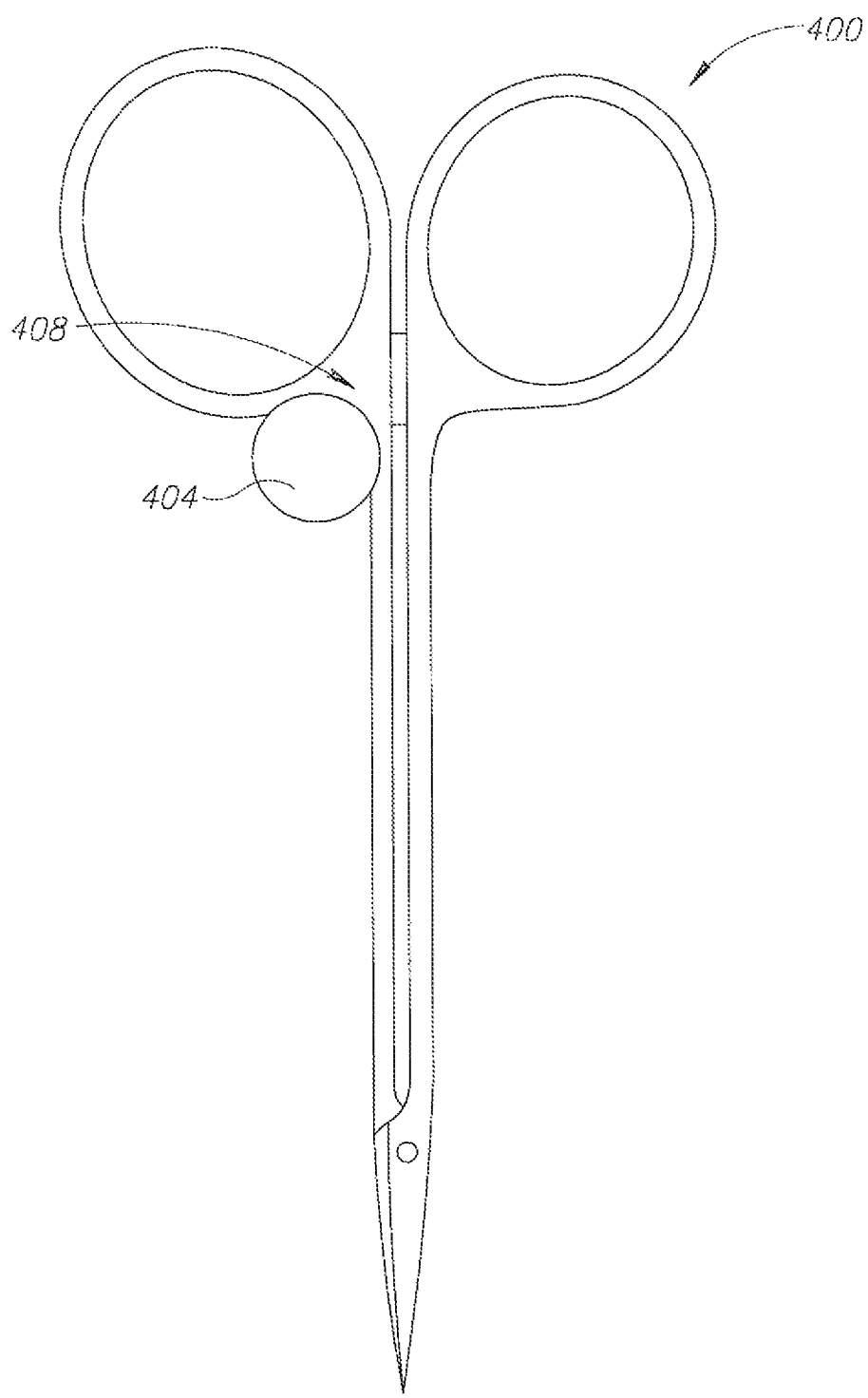
FIG. 4 is a schematic illustration of an exemplary tool with attached identification device, in accordance with the disclosure.

Referring now to FIG. 4, showing an exemplary tool with attached identification device.

FIG. 4 shows exemplary surgery scissors 400 and device 404 containing an identification device (not shown). In order to attach device 404 to tool 400, tool 400 has been retrofitted at area 408, so that its curve fits the perimeter of device 404.

Figure 5:
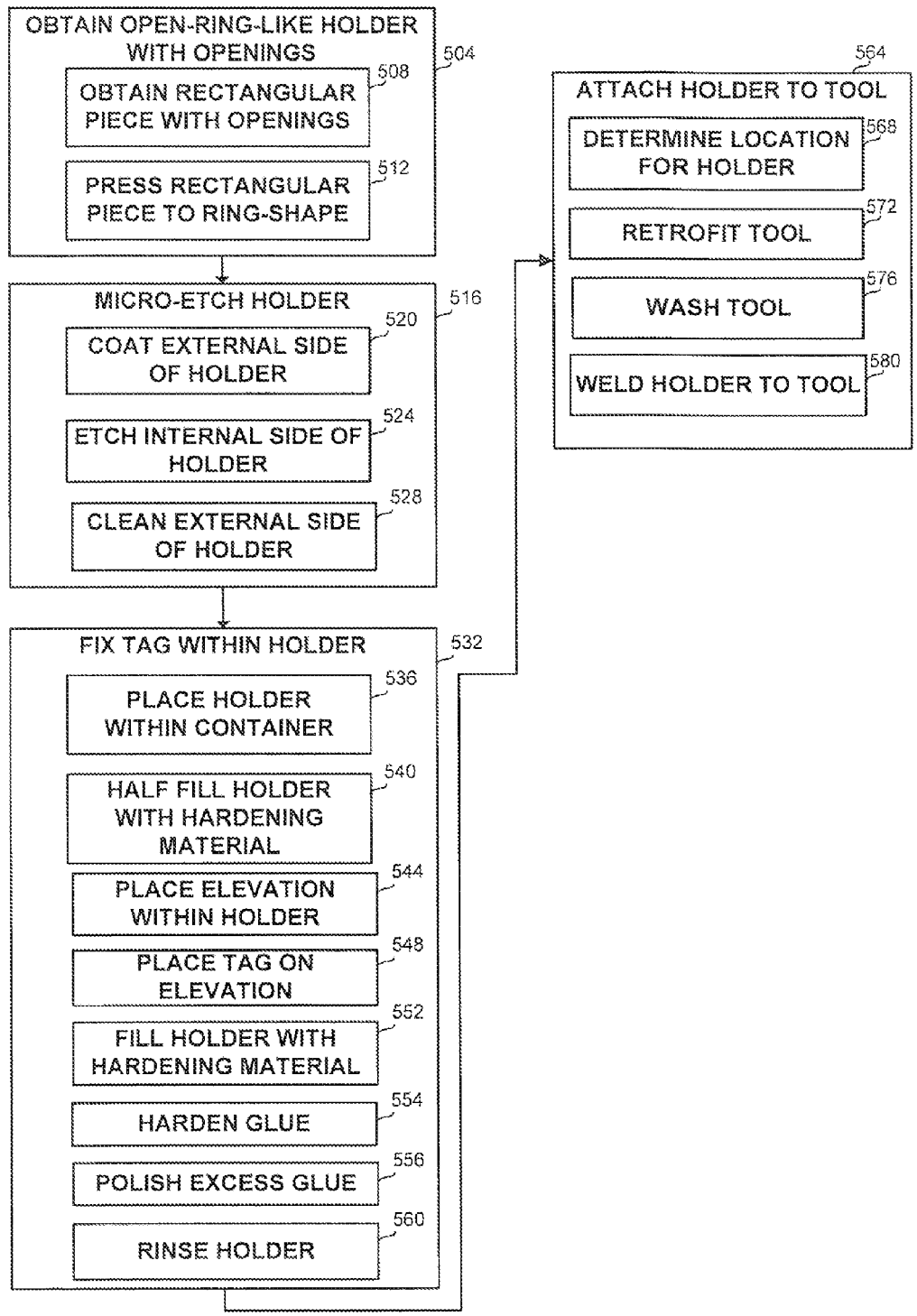
FIG. 5 is a flowchart of the main steps in a method for generating an identification tag and attaching the same to a surgery tool, in accordance with the disclosure.

Referring now to FIG. 5, showing a flowchart of the main steps in a method for generating an identification device to be attached to a holder, and attaching the identification device to a tool.

The method comprises step 504 for obtaining a holder shaped as a C-shaped stratum or an open ring, the holder having openings, step 516 for micro-etching the holder, step 532 for fixing or sealing a tag such as an RF tag within the holder, and step 564 for attaching the holder to a tool.

Step 504 for obtaining an open-ring-like holder with slots or other openings, optionally comprises step 508 for obtaining a stratum such as a rectangular piece with openings such as the exemplary embodiments shown in FIG. 1A or FIG. 1B, and step 512 for curving the rectangular piece along its long side into a ring shape with an opening, or a C shape. Curving can be carried out by pressing the rectangular piece.

Micro-etching step 516 optionally comprises attaching a coating layer to the external surface of one or more holders on step 520. The coating can be attached for example by threading the holders on an instrument that exposes only the external surface of each holder, and does not expose its opening. The external side of the holders can then be coated with glue, a silicone wrap or another coating.

Then on step 524 the internal surface of the holder, including the opening are micro-etched by letting etching fluid flow through the holder.

On optional step 528 the external surface of the holder is exposed by cleaning or otherwise removing the coating placed on step 520.

Tag fixing step 532 optionally comprises optional step 536 for placing the holder within a container, such as a silicone container. The holder is placed within the container on one of curved rims. On step 540 the holder, within the container, is filled to about half its height with hardening material such as glue, which is used in liquid state and later hardens into solid state. On optional step 544, an elevating component such as a bumper is placed within the container, and on step 548 the tag is placed on the bumper.

On step 552 the holder is filled to its rim with the hardening material, so as to cover the tag with the hardening material. On optional step 554 the hardening material is hardened, thus becoming solid and fixing the tag within the holder. On optional step 556 the excess hardening material is removed for example by polishing the external side and top side of the holder, and on step 560 the holder is rinsed from left polishing particles. The holder, together with the tag, the hardened glue and optionally the bumper are referred to as an identification device.

In order to attach the identification device to the tool on step 564, first a location has to be determined for placing the holder on the tool on step 568. It will be appreciated that step 568 can be performed once for any type of tool, and is not necessarily repeated for each specific tool.

On optional step 572 the tool is retrofitted at the determined location in order to adapt it to the identification device. Retrofitting may include milling or otherwise removing small parts in order to make the surface more rough and this more receptive for welding, and in order to adapt the shape of the tool at the determined area to the shape of the identification device.

On optional step 576 the tool is rinsed from the milling process, and on Step 580 the identification device is welded to the tool.

The disclosed identification device, and the method for preparing and attaching the identification device provide for attaching a tag such as an RF tag to a surgical tool, in order to enable computerized control and maintenance of tools used in surgical environments. The identification device is bio compatible and resistant to all process which the tools undergo. It will be appreciated that the disclosed identification device and methods can be used for other environments as well and are not limited to surgery tools and environments.

It will also be appreciated that many of the steps and processes can be performed in alternative manners, alternative materials or alternative processes without deviating from the disclosure.

It will be appreciated by persons skilled in the art that the present disclosure is not limited to what has been particularly shown and described hereinabove. Rather the scope of the present disclosure is defined only by the claims which follow.

What is claimed is:

1. An identification device adapted to be attached to a tool, comprising:
    a holder formed as a curved stratum pressed to form a ring shaped enclosure enclosing a void, the holder having an external surface for attaching to the tool and an internal surface surrounding the void;
    an identification tag is embedded inside the void surrounded by the internal surface of the holder;
    hardening material that is used to fill the void fixing the identification tag so that it is surrounded by the internal surface of the holder;
    wherein the device is configured to identify the tool using the identification tag; and
    wherein the curved stratum surrounds the identification tag leaving an opening thereon to form an open ring.

2. The identification device of claim 1 further comprising an elevation component placed within the holder such as to avoid exposure of the identification tag from above or below the ring shaped enclosure formed by the curved stratum.

3. The identification device of claim 1 wherein the hardening material is a bio compatible material.

4. The identification device of claim 1 wherein the identification tag is a radio frequency (RF) tag.

5. The identification device of claim 1 wherein the external surface and the internal surface are substantially concentric.

6. The identification device of claim 1, wherein the identification device is made from a material that is attachable to the tool by a laser welding process.

7. The identification device of claim 1, wherein the internal surface of the holder is micro-etched.

8. An identification device adapted to be attached to a tool, comprising:
    a holder formed as a curved stratum pressed to form a substantially ring shaped enclosure enclosing a void, the holder having an external surface for attaching to the tool and an internal surface surrounding the void;
    an identification tag is embedded inside the void surrounded by the internal surface of the holder;
    hardening material that is used to fill the void fixing the identification tag so that it is surrounded by the internal surface of the holder;
    wherein the device is configured to identify the tool using the identification tag; and
    wherein the curved stratum has a C-shaped cross-section.

* * * * *